United States Patent [19]

Gaffar

[11] Patent Number: 4,816,245

[45] Date of Patent: Mar. 28, 1989

[54] ANTIPLAQUE/ANTIGINGIVITIS METHOD USING CERTAIN POLYPHOSPHONIC ACIDS

[75] Inventor: Abdul Gaffar, Somerset, N.J.

[73] Assignee: Colgate-Palmolive Company, New York, N.Y.

[21] Appl. No.: 102,269

[22] Filed: Sep. 25, 1987

Related U.S. Application Data

[63] Continuation of Ser. No. 885,735, Jul. 21, 1986, abandoned, which is a continuation of Ser. No. 745,042, Jun. 17, 1985, abandoned, which is a continuation-in-part of Ser. No. 566,367, Dec. 28, 1983, abandoned.

[51] Int. Cl.⁴ ................................................ A61K 7/16
[52] U.S. Cl. ...................................... 424/57; 514/902
[58] Field of Search ..................... 424/49, 57; 514/902

[56] References Cited

U.S. PATENT DOCUMENTS 3,914,406 10/1975 Yankell ................................. 424/52
4,139,477 2/1979 Gaffar ................................... 424/52
4,427,652 1/1984 Gaffar ................................... 424/52

FOREIGN PATENT DOCUMENTS 1372199 10/1974 United Kingdom .

OTHER PUBLICATIONS

J. Dent. Res. 58(3)—1134–1145 (1979)—Anbar et al.
Chem. Abst. 82 (5): 25739(d) (1975) Anbar et al.
Chem. Abst. 82(25): 16476(t) (1975) Anbar et al.

Primary Examiner—Douglas W. Robinson
Attorney, Agent, or Firm—Murray M. Grill; Robert L. Stone

[57] ABSTRACT

A method of inhibiting human dental plaque and gingivitis involving regular application to the oral cavity of an oral composition containing an effective placque- and gingivitis-inhibiting amount of polyvinyl phosphonic acid or salt thereof having a number average molecular weight of about 4,000 to 9,100.

20 Claims, No Drawings

ANTIPLAQUE/ANTIGINGIVITIS METHOD USING CERTAIN POLYPHOSPHONIC ACIDS

This application is a continuation of application Ser. No. 885,735, filed July 21, 1986, now abandoned, which is a continuation of application Ser. No. 745,042, filed June 17, 1985, now abandoned, which was a continuation-in-part of abandoned application Ser. No. 566,367, filed Dec. 28, 1983, now abandoned.

This invention relates to the use of non-antibacterial agents and oral compositions for promoting human oral hygiene, and especially to a method for treating, controlling or inhibiting both plaque and gingivitis, which latter is characterized by such symptoms as inflammation, bleeding, recession, and/or swelling of the gums. Types of gingivitis include afunctional gingivitis, gingivitis marginal and cotton-roll gingivitis. Gingivitis leads to periodontitis.

The gums are seriously harmed by deposits of dental plaque, a combination of minerals and bacteria found in the mouth. The bacteria associated with plaque can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes.

*Actinomyces viscosus*, a gram positive rod, has been identified as implicated in the etiology of gingivitis Loeche et al "Bacteriology of human experimental gingivitis: effects of plaque and gingivitis sores," Infection and Immunity 21, 830–839 (1978). This organism attaches to tooth surfaces to form the dental plaque.

A multitude of materials have been previously proposed and employed for controlling plaque and gingivitis, but none have been entirely satisfactory. For example, some of such materials have been found to be unstable in the presence of the anionic surface active agents generally present in conventional oral preparations. A number of such materials such as the cationic quaternary ammonium agents exert an antibacterial function which undesirably tends to disrupt or destroy the normal microflora of the mouth and/or the digestive system.

U.S. Pat. No. 3,429,963 issued Feb. 25, 1969 to Leo Shedlovsky and assignee in common with the instant application proposes, among a number of other water soluble polyelectrolytes, the use of polyvinyl phosphonic acid (VPA polymer) or salts thereof for complexing calcium and inhibiting oral calculus, but the sole in vivo test described therein involved the supplying of drinking water containing a hydrolyzed copolymer of ethylene and maleic anhydride for ad libitum drinking by rats for a period of five days. This test is in the nature of a stoichiometric complexation of calcium and is unrelated to the threshhold effect occurring in actual oral use involving treatment of dental surfaces 1 to 3 times substantially daily for at least two weeks or lifetime. When subjected to such an actual use test, polyvinyl phosphonate acid has failed to significantly inhibit oral calculus.

U.S. Pat. No. 4,342,857 issued Aug. 3, 1982 to Abdul Gaffar, applicant herein, discloses and claims antigingivitis compositions containing a vinyl phosphonic acid/vinyl phosphonyl fluoride copolymer, but a number of scientists, authorities and/or jurisdictions object to administration of fluorinated materials to humans. U.S. Pat. No. 4,427,652 contains the same disclosure, being a division of U.S. Pat. No. 4,342,857.

British Patent No. 1,372,199 of Colgate-Palmolive Company, published Oct. 30, 1974, discloses anticaries and antiplaque oral compositions containing organic polymeric phosphonates having an M.W. (molecular weight) of from 1000 to 100,000 or more. Working data in the examples relate solely to inhibition of bacterial adhesion and growth by polyalkene polyphosphonates, but mention is made of "Homopolymeric sodium vinyl phosphonate (M.W. 20,000)" among "Other suitable materials." It may be assumed that this value of M.W. is a weight average (M.W.$_w$), corresponding to a number average (M.W.$_n$) of about 15,200. It has been found however, that polyvinyl phosphonic acids (VPA polymer) with an M.W.$_n$ of about 9,300 or more are substantially ineffective for inhibiting bacterial adhesion leading to dental plaque and gingivitis.

It is an object of this invention to provide an antiplaque/antigingivitis method which will not be subject to one or more of the above deficiencies and objections. Other objects and advantages will appear as the description proceeds.

The attainment of the above objects is made possible by my discovery that VPA polymer and its salts with an M.W.$_n$ of about 4,000 to 9,100 effectively interfere with or inhibit the attachment of *Actinomyces viscosus* and *S. Mutans* to saliva coated hydroxyapatite (HAP) beads. This is a reliable indication that the agent would interfere with the attachment of the organism to tooth surfaces, should reduce plaque, and hence reduce or inhibit gingivitis. Such antigingivitis activity has in fact been corroborated by an in vivo test on beagles as more fully discussed below.

This invention accordingly includes a method of inhibiting human dental plaque and gingivitis comprising applying to the human oral cavity a composition containing a dentally acceptable oral vehicle and an effective plaque- and gingivitis-inhibiting amount of polyvinyl phosphonic acid or an orally acceptable salt thereof having an M.W.$_n$ of about 4,000 to 9,100.

The VPA polymer of this invention should preferably have a number average molecular weight (obtained by GPC-gel permeation chromatography) of about 4,000 to 9,100, more preferably about 6,000 to about 8,900, and may be prepared in known manner by polymerizing vinyl phosphonyl dichloride under substantially anhydrous conditions in the presence of a free radical catalyst, and then mixing the resulting polymer with water to hydrolytically convert the vinyl phosphonyl dichloride units in the polymer to VPA units. The resulting polymer is in free acid form and may desirably be converted to salt form by treatment with any orally acceptable cation—providing base such as alkali metal (e,g, sodium or potassium), ammonium, $C_{1-18}$ mono-, di- and tri-substituted ammonium, (e.g. alkanol substituted ammonium, such as mono-, di- and tri-ethanolammonium), organic amines, etc. It will be understood that the mono- and di- salt forms of the polymer are the equivalent of the free acid form and that the term "water soluble" applicable to all such forms is inclusive of readily water dispersible forms thereof in the usual use concentrations.

It will also be understood that the VPA polymer may also contain minor proportions, i.e. preferably less than about 10 wt. %, more preferably less than about 5 wt. %, most preferably less than about 2 wt. %, of units derived from other non-fluorinated ethylenically unsaturated monomers which, in type and amount, are nontoxic and do not interfere with the desired water soluble and antigingivitis activities of the polymer. Other such monomers may, for example, include olefins such as ethylene, propylene, isopropylene, butylene and isobutylene, vinyl lower alkyl ethers such as vinyl methyl, ethyl and isobutyl ethers, alpha, beta unsaturated carboxylic acids and their lower alkyl and substituted lower alkyl esters such as acrylic, methacrylic, aconitic, maleic and fumaric acids and their methyl, ethyl, isobutyl and dimethylaminoethyl esters, allyl alcohol and acetate, vinyl and vinylidene halides, vinyl lower alkanoic acid esters such as vinyl acetate and butyrate, acrylamide and methacrylamide and N-lower alkyl and N,N-dilower alkyl substituted derivatives thereof, and the like.

The concentration of the VPA polymeric antiplaque agent in oral compositions can range widely, typically upwards of about 0.0% by weight with no upper limit except as dictated by cost or incompatibility with the vehicle, Generally, concentrations of about 0.01% to about 10%, preferably about 0.1% to about 8.0%, more preferable about 0.5% to about 5.0% by weight are utilized. Oral compositions which in the ordinary course of usage could be accidentally ingested preferably contain concentrations in the lower portions of the foregoing ranges.

In certain highly preferred forms of the invention, the oral composition may be substantially liquid such as mouthwash or rinse. Such preparations generally contain a humectant and the vehicle is typically a water-alcohol mixture. Generally, the ratio of water to alcohol is in the range of from about 1:1 to about 20:1 preferably from 3:1 to 20:1 and most preferably about 17:3% by weight. The total amount of water-alcohol mixture in this type of preparation is typically in the range of from about 70 to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a lower pH without substantially decalcifying dental enamel.

Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations contains polishing material. Examples of polishing materials are water-insoluble sodium metaphosphate, potassium metaphosphate tricalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof. Preferred polishing materials include crystalline silica having particle sizes of up to 5 microns a mean particle size of up to 1.1 microns, and a surface area of up to 50,000 cm$^2$/gm., silica gel, complex amorphous alkali metal aluminosilicate, hydrated alumina, dicalcium phosphate.

Alumina, particularly the hydrated alumina sold by Alcoa as C333, which has an alumina content of 64.9% by weight, a silica content of 0.008%, a ferric oxide content of 0.003%, and a moisture content of 0.037%, at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "insoluble" polishing materials are anionic in character and also include small amounts of soluble material. Thus, insoluble sodium metaphosphate may be formed in any suitable manner, as illustrated by Thorpe's Dictionary of Applied Chemistry, Volume 9, fourth Edition, pp. 510–511. The and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than 37 microns.

The polishing material is generally present in amounts ranging from about 10 to about 99% by weight of the oral preparation. Preferably, it is present in amounts ranging from about 10 to about 75% in toothpaste, and from about 70 to about 99% in toothpowder.

In the preparation of toothpowders, it is usually sufficient to admix mechanically, e.g., by milling, the various solid ingredients in appropriate quantities and particle sizes.

In pasty oral preparations the above-defined combination of the antigingivitis agent and polishing material should be compatible with the other components of the preparation. Thus, in a toothpaste, the liquid vehicle may comprise water and humectant typically in an amount ranging from about 10 to about 90% by weight of the preparation. Glycerine, sorbitol, or polyethylene glycol may also be present as humectants or binders. Particularly advantageous liquid ingredients are polyethylene glycol and polypropylene glycol. Also advantageous are liquid mixtures of water, glycerine and sorbitol.

In clear gels where the refractive index is an important consideration, about 3–30% by weight of water, 0 to about 80% by weight of glycerine, and about 20–28% by weight of sorbitol is preferably employed. A gelling agent, such as natural or synthetic gums or gum-like materials, typically Irish moss, sodium carboxymethylcellulose, methyl cellulose, hydroxyethyl cellulose, gum tragacanth, polyvinylpyrrolidone, starch, and preferably hydroxypropyl methyl cellulose and the Carbopols (e.g. 934,940 and 941), etcetera is usually present in toothpaste in an amount of up to about 10% by weight, preferably in the range of from about 0.5 to about 5%. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0 may also contain a surface active agent and/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, e.g. aluminum or lined lead, pump or other squeeze dispenser for metering out the contents, having a label describing it, in substance, as a toothpaste or dental cream.

The oral compositions of this invention may contain a non-soap synthetic sufficiently water soluble organic anionic or nonionic surfactant in concentrations generally ranging from about 0.05 to about 10, preferably about 0.5 to about 5, weight percent, to promote wetting, detersive and foaming properties. U.S. Pat. No. 4,041,149 discloses such suitable anionic surfactants in column 4, lines 31-38, and such suitable nonionic surfactants in column 8, lines 30-68 and column 9, lines 1-12 which passages are incorporated herein by reference thereto.

In certain forms of this invention a fluorine-providing compound is present in the oral preparation. These compounds may be slightly soluble in water or may be fully water-soluble. They are characterized by their ability to release fluoride ions in water and by substantial freedom from reaction with other components of the oral preparation. Among these materials are inorganic fluoride salts, such as soluble alkali metal, alkaline earth metal and heavy metal salts, for example, sodium fluoride, potassium fluoride, ammonium fluoride, Ca fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005 to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium mono-fluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013 to 0.1% and most preferably about 0.0013% by weight, of fluoride.

Various other materials may be incorporated in the oral preparations of this invention, subject to the above. Examples are whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed, also subject to the above. Examples of suitable flavoring constituents are flavoring oils, e.g., oils of spearmint, peppermint, wintergreen, sassafrass, clove, sage, eucalyptus, majoram, cinnamon, lemon and orange, and methyl salicylate. Suitable sweetening agents include sucrose, lactose, maltose, sorbitol, sodium cyclamate, perillartine, APM (aspartylphenylalanine, methyl ester) and saccharin. Suitably, flavor and sweetening agents may together comprise from about 0.1 to 5% or more of the preparation.

In the practice of this invention an oral composition according to this invention such as a mouthwash or toothpaste containing the antiplaque agent in an orally acceptable vehicle may be prepared by unifying the components in conventional manner, and applied to the gingiva and teeth regularly, substantially daily, e.g. from about 1 to 3 times daily or every second or third day, etc., at a pH of about 4.5 to about 9, generally about 5.5 to about 8.5, preferably about 6 to about 8, preferably for at least two weeks up to eight weeks or more or lifetime.

In the case of chewing gum and other products, the VPA active ingredients can be incorporated in any suitable manner during the usual manufacture of the product. For example, they can be incorporated in a warm gum base with stirring to distribute the same uniformly therein. They can also be added to the exterior or outer surfaces of a gum base in order to coat the base. The usual gum bases can be used, representative materials being jelutone, rubber latex, vinylite resins, etc., in addition to other usual materials such as plasticizers or softeners, sugar or other suitable carbohydrates such as glucose, sorbitol, etc.

The following examples are further illustrative of the nature of this invention but it is understood that the invention is not limited thereto. All amounts and proportions referred to herein and in the appended claims are by weight, and temperatures are in degrees C. unless otherwise indicated. The VPA polymer employed in these examples had a molecular weight ($M.W._w$) of about 10,700 employed in the form of the disodium salt. This $M.W._w$ corresponds to an $M.W._n$ of about 7,300 for this polymer.

EXAMPLE I

Adsorption of Sodium Polyvinyl Phosphonate to Dental Enamel

The adsorption of the polymer to enamel surfaces was measured in vitro. Human extracted, non-carious and non-filled molar teeth were cleaned by pumicing.

They were then polished with a rubber cup and polishing agent. They were mounted onto a rubber stopper via a nichrome wire which was tied through a hole in the roots. A sodium salt of polymer solutions at pH 7.0 were dispensed in polyethylene tubes. The teeth were submerged in the solution at 37° C. for 1 hour under a continuous agitation. Special care was taken to avoid the contact of solution with roots of the teeth. After one hour incubation, the teeth were removed and the solutions were analyzed for the amount of polymer left in the solution. The adsorption was calculated by a difference between amount initially added minus the amount left after exposing to teeth.

The concentration of the polymer in the solution was assessed by turbidimetric measurements using 5M $CaCl_2$ solution at pH 4.5. 1 cc. of $CaCl_2$ was added to 1 cc. of the polymer solution. The turbidity of resulting colloidal suspension at 500 nanometer proved to be proportional to the Polymer concentration ranging from 1 to 8 mgs/ml. A calibration curve was carried out with the known amount of the polymer.

TABLE 1

| | Results: | |
|---|---|---|
| Conc. of Poly-$Na_2VPA$ (mg/ml) | Amt. Left After Tooth Immersion (mg/ml) | Amt. Adsorbed to Teeth (mg/ml) |
| 2 | 0.4 | 1.6 |
| 3 | 0.7 | 2.3 |
| 4 | 1.1 | 2.9 |
| 5 | 1.6 | 3.4 |
| 6 | 2.4 | 3.6 |
| 7 | 3.3 | 3.7 |

The data indicated a significant adsorption of the VPA polymer to enamel surfaces.

EXAMPLE II

Effect of Polymer on the Adsorption of Actinomyces Viscosus T14 on Saliva Coated Hydroxyapatite (HAP) Beads 80 mgs. of HAP beads were pre-coated with human saliva (blood type A) for 12 hours. The beads were washed and pretreated with the solution of the polymer at pH 7.0 for 5 minutes. The treated beads were washed with a buffer consisting of 0.05 M KCl 1 mM $PO_4$, 1 mM $CaCl_2$ and 0.1 mM $MgCl_2$ at pH 6.0. This buffer simulates saliva inorganic constituents.

For the adsorption studies the mixture (1.0 ml) contained $5 \times 10^7$ $H^3$ thymidine labelled bacteria (*Actinomyces viscosus*), 30 mg saliva coated beads (S HAP) and the buffer. The mixture was continuously shaken at room temperature for 2 hours. The beads were allowed to settle for one minute and the supernatant which contained unadsorbed cells was removed. The radioactivity was measured via liquid scintillation counts. Portions of known $H^3$ labelled cells were counted in a similar manner so that counts per minute may be related to bacterial cell number. Control bacterial suspensions were incubated with S-HAP beads.

TABLE II

Results:
Effects of Pre-Treating Saliva Coated HAP Beads With Polyvinyl Phosphonate on Adsorption of Bacteria
*A. Viscosus* LY7

| S-HAP Treatment | Cells Adsorbed ($\times 10^7$) per 20 mg S-HAP | % Relative to Buffer KCl |
|---|---|---|
| Buffered KCl | 3.88 ± 0.04 | 100 |
| 1% $Na_2VPA$ Polymer | 1.23 ± 0.05 | 32 |
| 0.1% $Na_2VPA$ Polymer | 3.54 ± 0.16 | 91 |
| 0.01% $Na_2VPA$ Polymer | 3.55 ± 0.09 | 92 |

The results show that a pre-treatment of S-HAP with the polyvinyl phosphonate was significantly effective in inhibiting bacterial attachment.

EXAMPLE III

This study in 20 beagle dogs evaluated the effect of a placebo and a rinse containing 1% sodium salt of polyvinyl phosphonic acid on plaque/gingivitis for 4 weeks. The dogs were given complete prophylaxis to remove soft and hard dental deposits. A disclosing solution was used to insure the complete removal of dental deposits. The beagles were kept on a soft diet for 4 weeks. Group I (10 dogs) were then treated with the placebo rinse, while Group II was treated with the rinse containing the polymer. The treatment was done 1/day/5 days per week by applying 5-6 cc. of the rinse on all dentition. The study was double blind. Neither the evaluator nor the people involved in the treatments knew the assignments of rinses in the respective groups. The plaque and gingivitis was assessed via Loe and Silness index (*Acta Odontologica Scandinavica*, 21:551-555 (1963)).

TABLE III

| | | | Results: | | | |
|---|---|---|---|---|---|---|
| Mouth Rinse | N | Group | Plaque Index/Tooth - 4 Wks Post Treatment | % Change | Gingival Index 4 Wks Post Treatment | % Change |
| Placebo | 10 | I | 0.99 ± 0.23 | — | 0.91 ± 0.10 | — |
| 1% $Na_2VPA$ Polymer | 10 | II | 0.68 ± 0.23 | −31 | 0.73 ± 0.29 | −20 |

Compared to the placebo rinse, the polyvinyl phosphonate rinse significantly reduced plaque/gingivitis for four weeks.

The following examples of oral (mouthwash and toothpaste) formulations are further illustrative of this invention.

EXAMPLE IV

| | Wt. Percent |
|---|---|
| Glycerin | 10.0 |
| Ethanol | 10.0 |
| Pluronic F108* | 3.8 |
| Na Saccharin | 0.03 |
| Polyvinyl phosphonate | 1.0 |
| Flavor | 0.22 |
| Water to make | 100.00 |

*BAS F-Wyandotte block polymer nonionic surfactant containng about 20 wt. % polyoxypropylene chain of about 3250 M.W. and about 80 wt. % polyoxyethylene.

EXAMPLE V

| | Wt. Percent |
|---|---|
| Glycerin | 25.0 |

| | Wt. Percent |
|---|---|
| Carboxymethyl Cellulose | 1.3 |
| Sodium Benzoate | 0.5 |
| Na Saccharin | 0.2 |
| Silica | 30.0 |
| Sodium Lauryl Sulfate | 1.5 |
| Polyvinyl Phosphonate | 3.0 |
| Water to make | 100.0 |

This invention has been disclosed with respect to preferred embodiments and it will be understood that modifications and variations thereof obvious to those skilled in the art are to be included within the spirit and purview of this application and the scope of the appended claims.

I claim:

1. A method of inhibiting human dental plaque or gingivitis comprising applying to the human oral cavity a composition comprising a dentally acceptable oral vehicle and an effective plaque- or gingivitis-inhibiting amount of polyvinyl phosphonic acid having a number average molecular weight of about 4,000 to 9,1000 or orally acceptable salt thereof.

2. A method according to claim 1 wherein said composition contains about 0.01% to about 10% by weight of the polyvinyl phosphonic acid or salt thereof.

3. A method according to claim 1 wherein said composition contains about 0.5% to about 5% by weight of the polyvinyl phosphonic acid or salt thereof.

4. A method according to claim 1 wherein said composition is a mouthwash having a pH of about 4.5 to about 9 with an aqueous-alcohol vehicle.

5. A method according to claim 1 wherein said composition is a toothpaste having a pH of about 4.5 to about 9, with a liquid vehicle, a gelling agent and a dentally acceptable polishing agent.

6. A method according to claim 4 wherein said mouthwash contains about 0.01% to about 10% by weight of the polyvinyl phosphonic acid or salt thereof.

7. A method according to claim 5 wherein said toothpaste contains about 0.01% to about 10% by weight of the polyvinylphosphonic acid or salt thereof.

8. The method of claim 1 employing poly (disodium vinyl phosphonate).

9. The method of claim 2 employing poly (disodium vinyl phosphonate).

10. The method of claim 3 employing poly (disodium vinyl phosphonate).

11. The method of claim 4 employing poly (disodium vinyl phosphonate).

12. The method of claim 5 employing poly (disodium vinyl phosphonate).

13. The method of claim 6 employing poly (disodium vinyl phosphonate).

14. The method of claim 7 employing poly (disodium vinyl phosphonate).

15. A method according to claim 1 wherein said composition contains about 0.1% to about 8% by weight of the polyvinyl phosphonic acid or salt thereof.

16. A method according to claim 4 wherein said composition contains about 0.1% to about 8% by weight of the polyvinyl phosphonic acid or salt thereof.

17. A method according to claim 5 wherein said composition contains about 0.1% to about 8% by weight of the polyvinyl phosphonic acid or salt thereof.

18. A method according to claim 8 wherein said composition contains about 0.1% to about 8% by weight of the polyvinyl phosphonic acid or salt thereof.

19. A method according to claim 2 wherein said polyvinyl phosphonic acid has a number average molecular weight of about 6,000 to about 8,900.

20. A method according to claim 8 wherein said polyvinyl phosphonic acid has a number average molecular weight of about 6,000 to about 8,900.

* * * * *